(12) United States Patent
Fisher et al.

(10) Patent No.: US 6,887,682 B2
(45) Date of Patent: May 3, 2005

(54) CHAPERONIN AND OSMOLYTE PROTEIN FOLDING AND RELATED SCREENING METHODS

(75) Inventors: Mark T. Fisher, Prairie Village, KS (US); Paul A. Voziyan, Overland Park, KS (US)

(73) Assignee: University of Kansas Medical Center, Kansas City, KS (US)

(*) Notice: Subject to any disclaimer, the term of this patent is extended or adjusted under 35 U.S.C. 154(b) by 92 days.

(21) Appl. No.: 09/808,774

(22) Filed: Mar. 15, 2001

(65) Prior Publication Data

US 2002/0006636 A1 Jan. 17, 2002

Related U.S. Application Data

(60) Provisional application No. 60/189,362, filed on Mar. 15, 2000.

(51) Int. Cl.[7] .......................... C12P 21/06; C12P 21/02; G01N 33/53
(52) U.S. Cl. ...................... 435/68.1; 435/7.1
(58) Field of Search ................ 530/300, 350, 530/344, 420; 435/68.1, 69.1, 172.3, 7.1

(56) References Cited

PUBLICATIONS

Altamirano MM, Golbik R, Zahn R, Buckle AM, Fersht AR. Refolding chromatography with immobilized mini–chaperones. Proc Natl Acad Sci U S A. Apr. 15, 1997;94(8):3576–8.*
Altamirano MM, Garcia C, Possani LD, Fersht AR. Oxidative refolding chromatography; folding of the scorpion toxin Cn5. Nat Biotechnol. Feb. 1999;17(2):187–91.*
Gorovits BM, Horowitz PM. Conditions of forming protein complexes with GroEL can influence the mechanism of chaperonin–assisted refolding. J Biol Chem. Jan. 3, 1997;272(1):32–5.*
Roderich Brandsch, et al., GroE Dependence on Refolding and Holoenzyme Formation off 6–Hudroxy–D–NICOTINE Oxidase, *The Journal of Biological Chemistry*, Oct. 15, 1992, vol. 267, No. 29, pp. 20844–20849, USA.
George W. Farr, et al., Multivalent Binding of Nonnative Substrate Proteins by the Chaperonin GroEL, *Cell*, Mar. 3, 2000, vol. 100, pp. 561–573, USA.
Mark T. Fisher, On the Assembly of Dodecameric Glutamine Synthetase from Stable Chaperonin Complexes. *The Journal of Biological Chemistry*, Jul. 5, 1993, vol. 268, No. 19, pp. 13777–13779, USA.
Mark T. Fisher, Promotion of the in Vitro Renaturation of Dodecameric Glutamine Synthetase from *Escherichia coli* in the Presence of GroEL (Chaperonin–60) and ATP, *Biochemistry*, Apr. 28, 1992, pp. 3955–3963, USA.
Boris M. Gorovits, et al., Rhodanese folding is controlled by the partioning of its folding intermediates, 1998, *Biochimica et Biophysica Acta*, 1382 120–128.

Sangita Phadtare, et al., Refolding and release of tubulins by a functional immobilied gro EL column, 1994, *Biochimica et Biophysica Acta*, 1208 189–192.
Kirk E. Smith, et al., Interactions between the GroE Chaperonins and Rhodanese, *The Journal of Biological Chemistry*, Sep. 15, 1995, vol. 270, No. 37, pp. 21517–21523, USA.
Jiu–Li Song, et al., Natural Osmolyte Trimethylamine N–Oxide Corrects Assembly Defects of Mutant Branched–chain α–Ketoacid Decarboxylase in Maple Syrup Urine Disease, *The Journal of Biological Chemistry*, Oct. 26, 2001, vol. 276, No. 43, pp. 40241–40246, USA.
Bryan C. Tieman, et al., A Comparison of the GroE Chaperonin Requirements for Sequentially and Structurally Homologous Malate Dehydrogenases, *The Journal of Biological Chemistry*, Nov. 30, 2001, vol. 276, No. 48, pp. 44541–44550. USA.
Paul V. Viitanen, et al., Complex Interactions between the Chaperonin 60 Molecular Chaperone and Dihydrofolate Reductase, *Biochemistry*, Jul. 1, 1991, vol. 30, 9716–9723, Wilmington, Delaware, USA.
Paul V. Viitanen, et al., Purified chaperonin 60 (groEL) interacts with the nonnative states of a multitude of *Escherichia coli* proteins, *Protein Science*, 1992, 1, 363–369, Cambridge University Press, USA.
Paul A. Voziyan, et al., Chaperonin–assisted folding of glutamine synthetase under nonpermissive conditions: Off–pathway aggregation propensity does not determine the co–chaperonin requirement, *Protein Science*, 2000, 9:2405–2412, Cambridge University Press, USA.
Paul A. Voziyan, et al., Polyols Induce ATP–Independent Folding of GroEL–Bound Bacterial Glutamine Synthetase, *Archives of Biochemistry and Biophysics*, Jan. 15, 2002, vol. 397, No. 2, pp. 293–297, USA.
Paul A. Voziyan, et al., Refolding a Glutamine Synthetase Truncation Mutant in Vitro: Identifying Superior Conditions Using a Combination of Chaperonins and Osmolytes, *Journal of Pharmaceutical Sciences*, Aug. 2000, vol. 89, No. 8, pp. 1036–1045, USA.

(Continued)

Primary Examiner—Jon Weber
Assistant Examiner—Sheridan Snedden
(74) Attorney, Agent, or Firm—Stinson Morrison Hecker LLP

(57) ABSTRACT

The invention describes an inexpensive in vitro protein folding process for preventing large scale protein misfolding and aggregation, for concentrating aggregation prone chaperonin-protein folding intermediates in a stable non-aggregating form, and for rapidly screening these stable concentrates for the best folding solution conditions. The process comprises: (1) the formation of a chaperone-substrate complex and (2) the release of the substrate using a broad array of folding solutions containing different osmolyte ions, detergents, gradients of ionic strength and pH or other commonly used folding additives. Specifically, when the chaperonin/osmolyte protein process was applied to identify and optimize GSΔ468 bacterial glutamine synthetase mutant refolding conditions that otherwise cannot be folded in vitro by commonly used techniques, 67% of the enzymatic activity was recovered.

29 Claims, 13 Drawing Sheets

PUBLICATIONS

Aijun Wang, et al., A Naturally Occurring Protective System in Urea–Rich Cells: Mechanism of Osmolyte Protection of Proteins against Urea Denaturation, *Biochemistry*, 1997, 36m 9101–9108, USA.

Jue D. Wang, et al., GroEL–GroES–mediated protein folding requires an intact central cavity, *Proc. Natl. Acad. Sci. USA*, Oct. 1998, vol. 95, pp. 12163–12168, USA.

Frank Weber, et al., The oligomeric structure of GroEL/GroES is required for biologically significant chaperonin function in protein folding, *Nature Structural Biology*, 1998 Nature America Inc., vol. 5 No. 11, pp. 977–985, USA.

Wang Zhi, et al., Renaturation of citrate synthase: Influence of dentaurant and folding assistants, 1992, *Protein Science*, I, 522–529, USA.

* cited by examiner

Glutamine Synthetase

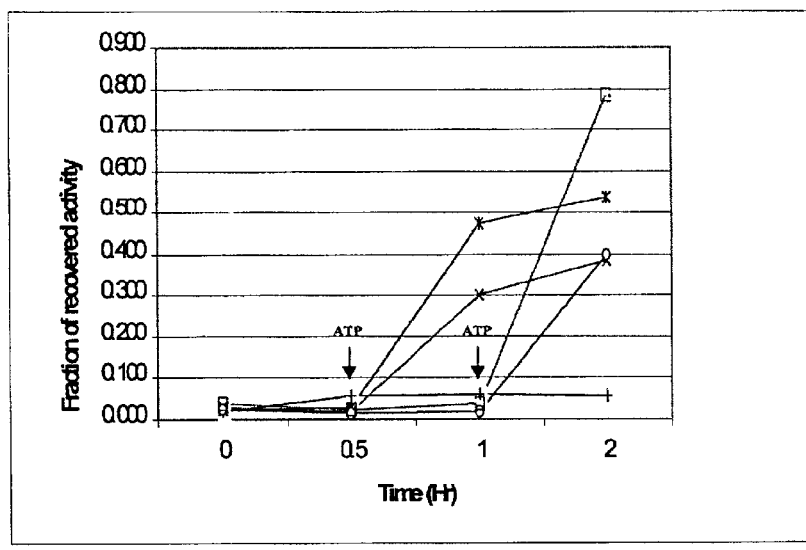

"+" Represents blank beads, all other symbols represent EL-beads.

*(+) GS refolding with blocked beads alone no chaperonins present.*

*(X) incubation of GS-immobilized chaperonin complex for ½ hour before 5 mM and 10 mM MgCl₂ added. Activity was followed over two hours.*

*(Star \*) incubation of GS-immobilized chaperonin complex for ½ hour before 5 mM and 10 mM MgCl₂ added. The beads were reused from previous (X) experiment.*

*(Open circle)– Refolding of GS from immobilized chaperonin system on beads – this experiment shows that the activity of GS is recovered after the chaperonin-GS complex was incubated for one hour. At that time, 5 mM ATP and 10 mM MgCl2 was added. Activity was monitored one hour later.*

*(Open square) – same as open circle only refolding of GS from immobilized chaperonin beads with a second replicate. This experiment shows that the immobilized chaperonin system can be reused with comparable results after the Chaperonin-GS complex was incubated for one hour.*

FIGURE 6

CHAPERONIN AND OSMOLYTE PROTEIN FOLDING AND RELATED SCREENING METHODS

This application incorporates and claims the benefits and priorities of U.S. provisional application No. 60/189,362 filed on Mar. 15, 2000.

FIELD OF THE INVENTION

This invention relates to a method of in vitro protein folding. More particularly, the method employs both chaperonins and osmolytes to optimize protein folding as well as to aid in the screening for optimal folding solution conditions.

BACKGROUND OF THE INVENTION

Efficient refolding of proteins in vitro is an important problem in protein structural analysis and biotechnological manufacturing of pharmaceutical products. Because of their inherent ability to rapidly overexpress proteins to high yields, bacterial systems are the organisms of choice for protein mass production. Unfortunately, overexpression of foreign and, especially, mutant proteins often leads to the development of large intracellular aggregates or inclusion bodies (Rudolph, R and Lilie, H. (1996) *FASEB J.* 10, 49–56; Guise, A. D., West, S. M., and Chaudhuri, J. B. (1996) *Mol. Biotechnol.* 6, 53–64, the disclosures of which are incorporated herein by reference). In some cases, the proper intracellular folding of the overexpressed proteins can be enhanced by lowering the cell growth temperature, co-expressing molecular chaperones, or introducing low molecular weight additives (Kujau, M. J., Hoischen, C., Riesenberg, D., and Gumpert, J. (1998) *Appl. Microbiol. Biotechnol.* 49, 51–58; Tate, C. G., Whiteley, E., and Betenbaugh, M. J. (1999) *J. Biol-Chem.* 274, 17551–17558; Minning, S., Schmidt-Dannert, C., Schmid, R. D. (1998) *J. Biotechnol.* 66, 147–156, the disclosures of which are incorporated herein by reference). More often, however, investigators are forced to rely on in vitro folding methods to denature (also known as "deactivate") and then refold (also known as "reactivate") aggregated proteins. A number of in vitro approaches have been developed to minimize protein aggregation and enhance proper refolding. Among those are: (1) the addition of osmolytes and denaturants to refolding buffer (Tate, C. G., Whiteley, E., and Betenbaugh, M. J. (1999) *J. Biol-Chem.* 274, 17551–17558; Plaza-del-Pino, I. M. and Sanchez-Ruiz, J. M. (1995) *Biochemistry* 34, 8621–8630, Frye, K. J. and Royer, C. A. (1997) *Protein. Sci.* 6: 789–793, the disclosures of which are incorporated herein by reference); (2) the use of the combinations of different molecular chaperones (Thomas, J. G., Ayling, A., and Baneyx, F. (1997) *Appl. Biochem. Biotechnol.* 66, 197–238; Buchberger, A., Schroder, H., Hesterkamp, T., Schonfeld, H. J., and Bukau, B. (1996) *J. Mol. Biol.* 261, 328–233; Veinger, L., Diamant, S., Buchner, J., and Goloubinoff, P. (1998) *J. Biol. Chem.* 273, 11032–11037, the disclosures of which are incorporated herein by reference); (3) immobilization of folding proteins to matrices and matrix-bound chaperonins (Stempfer, G., Holl-Neugebauer, B., and Rudolph, R. (1996) *Nat. Biotechnol.* 14, 329–334; Altamirano, M. M., Golbik, R., Zahn, R., Buckle, A. M., and Fersht, A. R. (1997) *Proc. Natl. Acad. Sci. USA* 94, 3576–3578; Preston, N. S., Baker, D. J., Bottomley, S. P., and Gore, M. G. (1999) *Biochim. Biophys. Acta* 1426, 99–109, the disclosures of which are incorporated herein by reference); and (4) utilization of folding catalysts such as protein disulfide isomerase and peptidyl-prolyl cis-trans isomerase (Altamirano, M. M., Garcia, C., Possani, L. D., and Fersht, A. R. (1999) *Nat. Biotechnol.* 17, 187–191, the disclosure of which is incorporated herein by reference). Unfortunately, because of the diversity of the protein folding mechanisms, there is no universal procedure for protein folding and folding conditions have to be optimized for each specific protein of interest. Therefore, there is always a need for new and more versatile folding techniques. This invention involves a novel protein folding procedure that combines the use of the GroE chaperonins and cellular osmolytes.

Because of its ability to bind many different protein folding intermediates, it was thought that the bacterial GroE chaperonin system could provide a general method to refold misfolded proteins. Chaperonin GroEL is a tetradecamer of identical 57 kDa subunits that possesses two large hydrophobic sites capable of binding to transient hydrophobic protein folding intermediates. The hydrophobic binding site undergoes the multiple cycles of exposure and burial driven by the ATP binding and hydrolysis and the co-chaperonin GroES binding and dissociation. Accordingly, the protein folding intermediates can undergo multiple rounds of binding to and release from the GroEL until they achieve the correctly folded state (for review, see Fenton, W. A. and Horwich, A. L. (1997) *Protein Sci.* 6, 743–760, the disclosure of which is incorporated herein by reference). Besides simple prevention of non-productive aggregation, chaperonins may also influence the conformation of the folding intermediates, actively diverting them to a productive folding pathway (Fedorov, A. N. and Baldwin, T. O. (1997) *J. Mol. Biol.* 268, 712–723; Shtilerman, M., Lorimer, G., and Englander, S. W. (1999) *Science* 284, 822–825, the disclosures of which are incorporated herein by reference). However, despite the general nature of chaperonin-protein interactions, there are many proteins that, for reasons that are currently unknown, cannot fold correctly from the bacterial chaperonin system.

The addition of osmolytes often results in an observed increase in stability of the native structure for some proteins. The stabilization effect is observed with various osmolytes and small electrolytes such as sucrose, glycerol, trimethylamine N-oxide (TMAO), potassium glutamate, arginine and betaine (Wang, A. and Bolen, D. W. (1997) *Biochemistry* 36, 9101–9108; De-Sanctis, G., Maranesi, A., Ferri, T., Poscia, A., Ascoli, F., and Santucci, R. (1996) *J. Protein. Chem.* 15, 599–606; Chen, B. L. and Arakawa, T. (1996) *J. Pharm. Sci.* 85, 419–426; Zhi, W., Landry, S. J., Gierasch, L. M., and Srere, P. A. (1992) *Protein Science* 1, 552–529, the disclosures of which are incorporated herein by reference). This effect is based on the exclusion of osmolytes from hydration shells and crevices on protein surface (Timasheff, S. N. (1992) *Biochemistry* 31, 9857–9864, the disclosure of which is incorporated herein by reference) or decreased solvation (Parsegian, V. A., Rand, R. P., and Rau. D. (1995). *Methods. Enzymol.* 259, 43–94, the disclosure of which is incorporated herein by reference). In a series of quantitative studies, Wang and Bolen have shown that the osmolyte-induced increase in protein stability is due to a preferential burial of the polypeptide backbone rather than the amino acid side chains (Wang, A. and Bolen, D. W. (1997) *Biochemistry* 36, 9101–9108). Because native protein conformations are stabilized, proper folding reactions are also enhanced in the presence of osmolytes (Frye, K. J. and Royer, C. A. (1997) *Protein. Sci.* 6: 789–793; Kumar, T. K., Samuel, D., Jayaraman, G., Srimathi, T., and Yu, C. (1998) *Biochem. Mol. Biol. Int.* 46, 509–517; Baskakov, I.

and Bolen, D. W. (1998) *J. Biol. Chem.* 273: 4831–4834, the disclosures of which are incorporated herein by reference). Osmolytes usually affect protein stability and folding at physiological concentration range of 1–4 M (Yancey. P. H., Clark, M. E., Hand, S. C., Bowlus, R. D., and Somero, G. N. (1982) *Science* 217, 1214–1222, the disclosure of which is incorporated herein by reference). However, it is apparent that the degree of stabilization depends on both the nature of the osmolyte and the protein substrate (Sola-Penna, M., Ferreira-Pereira, A., Lemos, A. P., and Meyer-Fernandes, J. R. (1997) *Eur. J. Biochem.* 248, 24–29, the disclosure of which is incorporated herein by reference) and, in some instances, the initial aggregation reaction can actually accelerate in the presence of osmolytes (Voziyan, P. A. and Fisher M. T. (2000) *Protein Science*, Volume 9, 2405–2412).

Although GroE chaperonins and osmolytes have been used in the folding protocols separately, no studies have taught or suggested the feasibility of combining these two approaches. This invention demonstrates that the combination of chaperonins and osmolytes can provide a considerable advantage in assisting protein folding. Moreover, the method of the present invention can be applied as a more general technique for a rapid identification of the optimal folding solution conditions to achieve maximal yields of correctly folded protein. In particular, the initial off-pathway aggregation is avoided through formation of stable chaperonin-protein substrate complexes under the solution conditions that favor the maximum binding of the substrate to GroEL. These long-lived stable complexes are added to a series of different osmolyte solutions ("folding array") to identify the most efficient folding conditions for the protein substrate in question.

As a model, this invention examines the in vitro refolding of C-terminal truncation mutant of bacterial glutamine synthetase, GSΔ468. Unlike native glutamine synthetase ("GS"), this single amino acid truncation product folds to an intermediate that cannot be refolded to an active form by either chaperoning or osmolytes alone. However, the combination of chaperonins and a number of natural osmolytes allowed for the refolding of GSΔ468. Under the optimized conditions, close to 70% of mutant protein refolded to an active form, even at protein concentrations approaching 1 mg/ml.

Therefore, it is an object of this invention to provide an in vitro protein folding process for preventing large-scale protein misfolding and aggregation.

It is a further object to provide a protein folding process that concentrates aggregation prone chaperonin-protein folding intermediates in a stable non-aggregating form.

It is another object of this invention to provide a protein folding process that rapidly screens stable chaperonin-substrate intermediates for the best folding solution conditions.

To accomplish the above and related objects, this invention may be embodied in the detailed description that follows, together with the appended drawings and claims.

BRIEF DESCRIPTION OF THE FIGURES

FIG. 6 shows refolding of GS on chaperonin beads.

DETAILED DESCRIPTION OF THE INVENTION

I. Materials

Figure 1:
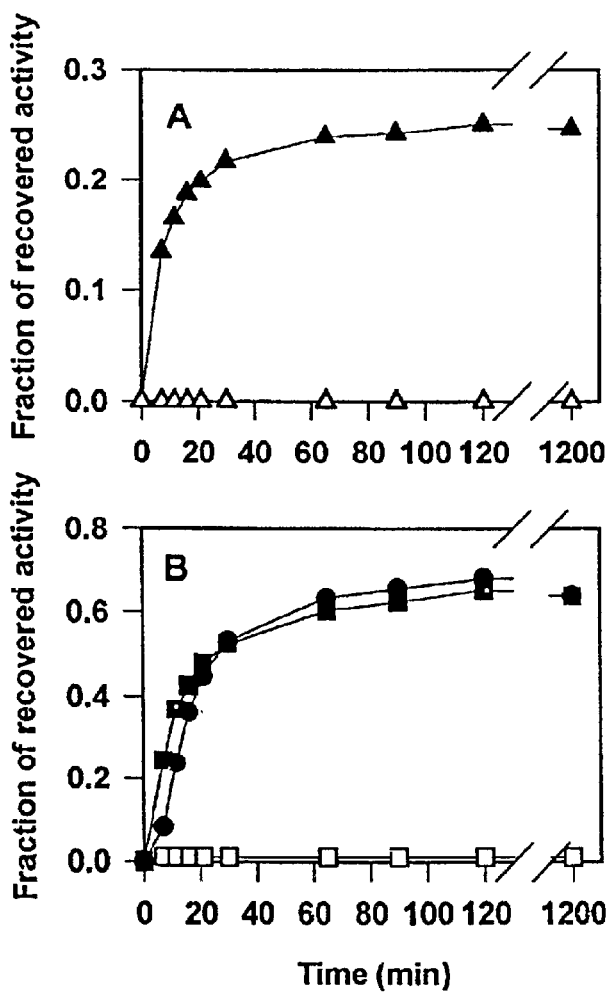
FIG. 1A and FIG. 1B show the kinetics of spontaneous and chaperonin-dependent renaturation of wild type and mutant GS.

As used herein, "protein" is defined as a polypeptide or polypeptide chain having a native or "active" form with a known biological function and a denatured form which does not exhibit the biological function of the native form.

As used herein, "chaperonin" is defined as any protein complex that binds to an unfolded polypeptide to facilitate the folding of said polypeptide to its biologically active state either independently or with the assistance of other elements. This definition specifically includes but is not limited to chaperonin systems from bacteria and bacteriophages, including mesophiles and thermophilic chaperoning. Similarly, as used herein, chaperonin includes but is not limited to chaperonins in any native or modified state, for example, single ring chaperoning, glutaldehyde cross-linked chaperonins or other chemically modified chaperoning.

As used herein, "unfolded", "denatured" and "inactive" are defined interchangeably to mean the characteristic of polypeptides which are no longer biologically active due, at lease in part, to not being in their native shape. As such, the terms include partially folded proteins, chemically unfolded proteins, thermally denatured proteins, pressure unfolded proteins, and oxidatively damaged proteins.

Urea was purchased from ICN Biochemical (Aurora, Ohio). Trimethylamine N-oxide dehydrate, potassium glutamate, betaine monohydrate, sarcosine hydrochloride, and ATP were from Sigma-Aldrich (St. Louis, Mo.). Glycerol and sucrose were purchased from Fisher Scientific (Pittsburgh, Pa.). All the above chemicals were over 99% pure. The other chemicals were of analytical grade.

Wild type GS was purified from *E. coli* as previously described (Fisher, M. T. and Stadtman, E. R. (1992) *J. Biol. Chem.* 267, 1872–1880, the disclosure of which is incorporated herein by reference). A single amino acid C-terminal truncation mutant GSΔ468 was a gift from Dr. R. Stoffel and Dr. Joe Villafranca (Stoffel, R. H., III. (1994) Thesis of Ph.D.

Dissertation. The Pennsylvania State University, the disclosure of which is incorporated herein by reference). The *E. coli* chaperonins, GroEL and GroES were isolated from overexpression *E coli* strains kindly provided by Drs. Edward Eisenstein and George Lorimer (respectively) and these proteins were purified essentially as described earlier (Fisher, M. T. (1992) *Biochemistry* 31, 3955–3963; Eisenstein, E., Reddy, P., and Fisher, M. T. (1998). *Methods. Enzymol.* 290, 119–135; Fisher, M. T. (1994) *J. Biol. Chem.* 269, 13629–13636, the disclosures of which are incorporated herein by reference). The GroEL purification protocol was modified by introducing an additional acetone precipitation step. After the Affi-Gel Blue treatment, GroEL samples were precipitated in 45% (v/v) acetone at room temperature for 5 minutes. The precipitate was centrifuged at 10,000 g for 30 minutes and, after the removal of acetone, re-suspended in 50 MM TrisHCl, 10 mM KCl, 5 mM $MgCl_2$ (pH 7.5). Residual protein aggregates and acetone were removed by a brief centrifugation followed by an extensive dialysis against the above mentioned buffer. The acetone precipitation step significantly improved quality (as measured by silver stained SDS-PAGE gels, tryptophan fluorescence, and second derivative analysis of the UV absorbance spectra) of those GroEL samples with minor impurities that could not be sufficiently purified by Affi-Gel Blue treatment alone. Acetone precipitation did not affect the functional properties of GroEL and can be used as an alternative to the ion-exchange chromatography in methanol for removing minor impurities from GroEL preparations (Todd, M. J. and Lorimer, G. H. (1998) *Methods. Enzymol.* 290, 136–144, the disclosure of which is incorporated herein by reference).

Molecular chaperones DnaK, DnaJ, and GrpE were purchased from Stress-Gene. Antibodies to *E. coli* GS were raised in sheep as described by Hohman and Stadtman (Hohman, R. J., Stadtman, E. R. (1978) *Biochem. Biophys. Res. Commun.* 82, 865–870, the disclosure of which is incorporated herein by reference).

II. Denaturation and Control Renaturation of GS

Wild type and mutant GS were denatured in solutions containing 50 mM Tris-HCl (pH 7.5), 5 mM EDTA, 10 mM DTT, and 8 M urea. The denaturation was performed for 4 hours at 0° C. The spontaneous refolding reaction from the denatured protein stock was initiated by a rapid 100-fold dilution of a small concentrated aliquot into either 50 mM Tris-HCl (pH 7.5), 5 mM $MgCl_2$, 50 mM KCl, 0.5 mM EDTA, and 10 mM DTT (buffer A), or into buffer A containing different additives at 37° C., followed by incubation at this temperature. Final GSΔ468 or wild type GS concentration was 0.3 μM.

For the chaperonin-dependent refolding, denatured GS subunits were diluted into buffer A containing either 1 μM GroEL or 1 μM GroEL and 2 μM GroES to form a GroEL-GS complex. After the incubation for 30 minutes at 37° C., either 5 mM ATP alone or ATP and different osmolytes were added and incubation continued for up to 40 hours. In some experiments, GroEL-GS complexes were concentrated using Centricon-30 centrifugation concentrators (Amicon, Inc., Beverly, Mass.) as described previously (Fisher, M. T. (1993) *J. Biol. Chem.* 268, 13777–13779, the disclosure of which is incorporated herein by reference), prior to the addition of ATP and/or osmolytes. Centrifugation was performed at 37° C. for 30 minutes. GS activity was determined by the glutamyl transferase assay (Woolfolk, C. A., Shapiro, B., and Stadtman, E. R. (1966) *Arch. Biochem. Biophys.* 116, 177–192, the disclosure of which is incorporated herein by reference).

III. Separation and Analysis of GS Renaturation Reaction Products

To characterize the time-dependent changes of the GS species during chaperonin renaturation, nondenaturing gradient gel electrophoresis was used as described before (Fisher, M. T. (1994) *J. Biol. Chem.* 269, 13629–13636). Briefly, the aliquots of GS renaturation reaction were applied to 8–25% polyacrylamide gradient gel (Pharmacia) at different times after the initiation of refolding. After the rapid (15–20 minutes) separation using the Pharmacia Phast system, the samples were electroblotted to nitrocellulose membrane and analyzed by Western blot using anti-GS antibody and the appropriate secondary antibody linked to alkaline phosphatase (Pierce Chemical Co.).

IV. Refolding of GSΔ468 from Concentrated Chaperonin Complexes

For the chaperonin-dependent refolding, denatured GSΔ468 was initially diluted into refolding buffer with either 2 μM GroEL alone or 2 μM GroEL and 4 μM GroES to a final GSΔ468 concentration of 0.3 μM. After the formation of GSΔ468 -chaperonin complex (10 minutes at 37° C.), samples were concentrated at 37° C. as previously described. Glycerol and ATP were added to respective concentrations of 4 M and 5 mM bringing final GSΔ468 concentration to 7 μM. For spontaneous refolding, the urea-unfolded GSΔ468 was rapidly diluted 100-fold into the refolding buffer (50 mM Tris-HCl, pH 7.5, 0.5 mM EDTA, 50 mM KCl, 5 mM $MgCl_2$) containing 4 M glycerol to a final concentration of 7 μM. Samples were incubated at 37° C. for up to 40 hours and GSΔ468 activity was determined.

V. Reactivation of Wild and Mutant GS

A. Native activity and refolding of wild type and mutant GS. Wild type GS and a single amino acid C-terminal truncation mutant GSΔ468 were produced in bacterial expression system YMC10/pgln6. The assembly of GS into active dodecamer involves swapping of the C-terminal regions of individual subunits and may be affected by truncation. Interestingly, both proteins purified to homogeneity from bacterial lysates were enzymatically active with the specific activity of the mutant GS comprising over 60% of wild type GS activity in a protein concentration range from 0.1 μM to 0.5 μM. Surprisingly, as shown in FIG. 1A, when the purified proteins were denatured in 8 M urea and refolded, the significant recovery of activity was detected only with wild type GS; the urea-denatured truncation mutant could not correctly reassemble and reactivate at all. More importantly, as depicted on FIG. 1B, the GroE chaperonins that enhance the refolding of wild type GS (Fisher, M. T. (1992) *Biochemistry* 31, 3955–3963), could not reactivate the GSΔ468 truncation mutant.

Figure 2:
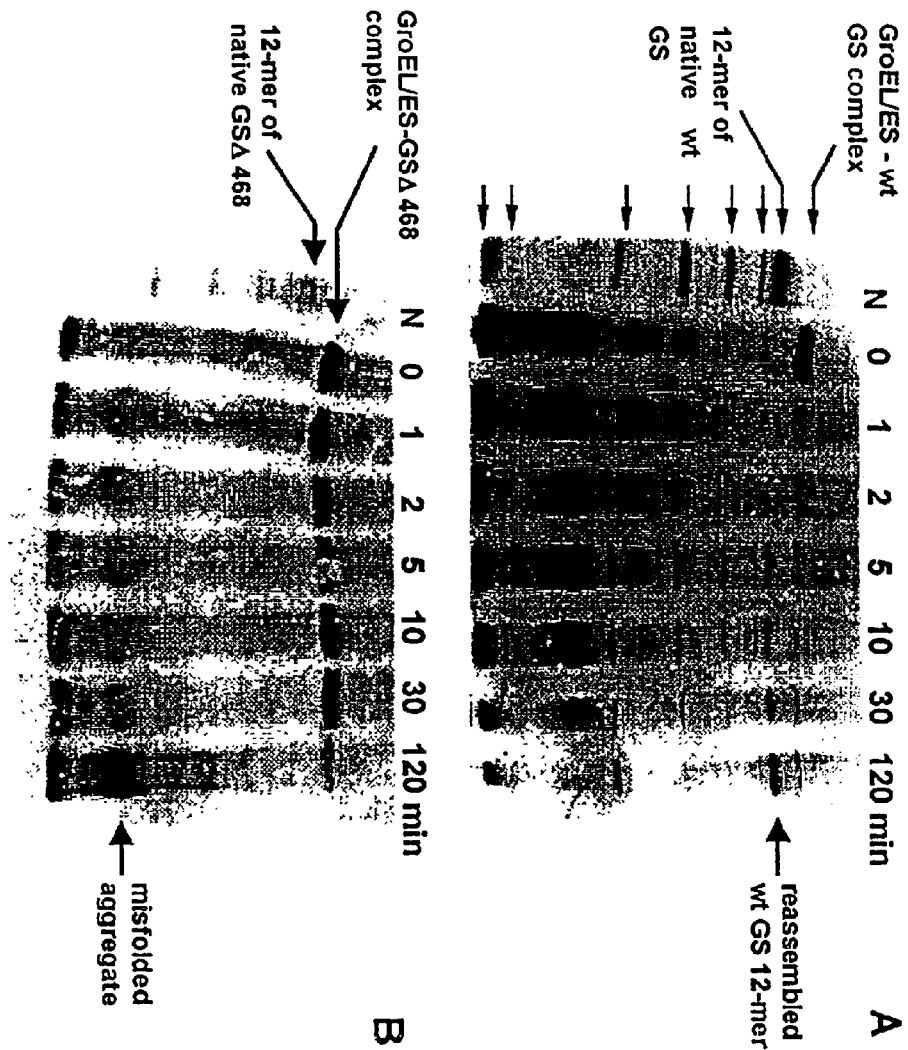
FIGS. 2A and 2B compare the assembly time of wild type GS and GSΔ468 in the presence of chaperonins. The set of arrows in FIG. 2 indicates the GS monomers, dimers, tetramers, and higher multimers produced by time-dependent association of native GS from the chaperonin.

B. Co-chaperonin refolding of wild and mutant GS. In order to determine why GSΔ468 failed to reactivate with chaperoning, a comparison was made between the time dependent assembly of wild type and mutant GS proteins using non-denaturing gel-electrophoresis and Western blot analysis (Fisher, M. T. (1994) *J. Biol. Chem.* 269, 13629–13636). FIG. 2A shows that upon the addition of GroES and ATP to the GroEL-wild type GS complex, this complex was no longer visible and the assembly of folding monomers into the native dodecamer was largely completed within 2 hours at 37° C. In contrast, FIG. 2B shows that the GSΔ468 -chaperonin complex remained visible throughout the time course of the experiment. Furthermore, unlike the wild-type GS, the truncation mutant did not form any native intermediate species after the dissociation from the chaperonin system. Instead, at the end of the time course, non-native aggregates, presumably aberrant dimers and tetramers of the mutant GS have accumulated (FIG. 2B, 120 minutes lane). Thus, GSΔ468 intermediates appear to bind to the chaperonin but are unable to attain an assembly-competent state after their dissociation from the chaperonin complex.

C. Chaperonin-dependent refolding of GSΔ468 in the presence of molecular chaperones. It has been demonstrated that a combination of molecular chaperones such as bacterial DnaK and GroE systems, can augment refolding of proteins that interact with the chaperonins yet fail to fold properly (Buchberger, A., Schroder, H., Hesterkamp, T., Schonfeld, H. J., and Bukau, B. (1996) *J. Mol. Biol.* 261, 328–233, Petit, M. A., Bedale, W., Osipiuk, J., Lu, C., Rajagopalan, M., McInerney, P., Goodman, M. F., Echols, H. (1994) *J. Biol. Chem.* 269, 23824–23829, the disclosures of which are incorporated herein by reference). However, the inclusion of the GroE and DnaK/DnaJ/GrpE systems with the GSΔ468 did not result in reactivation of the mutant protein. Change in the folding temperature of this system from 37° C. to 22° C. also failed to refold the truncation mutant.

D. Refolding of GSΔ468 in the presence of cellular osmolytes only. Solution additives such as low molecular weight osmolytes have been shown to induce protein folding in vitro, presumably by stabilizing protein native conformation (Wang, A. and Bolen, D. W. (1997) *Biochemistry* 36, 9101–9108). The present invention examined the effects of several cellular osmolytes on the refolding of GSΔ468. Of all the compounds, only glycerol and, to the lesser extent, sucrose, induced mutant GS refolding. Even so, as shown in Table 1, the recovery of activity under these conditions was very low.

TABLE 1

Refolding of GSΔ468 with GroE chaperonins and osmolytes at 37° C.

Activity recovered after 20 hours(fraction of native)

| Osmolyte | Osmolyte alone | with GroEL-ATP | with GroEL-GroES-ATP |
| --- | --- | --- | --- |
| 1M betaine | below assay detection limit | 0.13 ± 0.01 | 0.13 ± 0.01 |
| 1M sarcosine | << | 0.04 ± 0.01 | 0.20 ± 0.06 |
| 1M sucrose | 0.05 ± 0.02 | 0.36 ± 0.07 | 0.30 ± 0.07 |
| 0.5M KGlu | << | 0.09 ± 0.01 | 0.35 ± 0.06 |
| 1M TMAO | << | 0.22 ± 0.05 | 0.45 ± 0.09 |
| 4M glycerol | 0.18 ± 0.04 | 0.48 ± 0.08 | 0.47 ± 0.09 |

E. Chaperonin-Dependent Refolding of GSΔ468 in the Presence of Cellular Osmolytes.

However, when osmolytes were added to the chaperonin-GSΔ468 complex, a dramatic synergistic enhancement of protein reactivation was observed. After the formation of GSΔ468-chaperonin complex (10 minutes at 37° C.), respective osmolyte and 5 mM ATP were added. Samples were incubated at 37° C. for 20 hours and GSΔ468 activity was determined as described herein. Final GSΔ468 concentration was 0.3 μM. The data in Table 1 represent the mean ± standard deviation of three separate experiments. Not all the tested osmolytes gave the same results. Curiously, the addition of TMAO, potassium glutamate, betaine, and sarcosine worked only with the chaperonins i.e., neither folding enhancer alone produced any effect. This indicates that, in some cases, osmolyte enhanced refolding could only occur from the preexisting chaperonin-GSΔ468 complex.

For some of the osmolytes (TMAO, potassium glutamate, and sarcosine) the GSΔ468 reactivation increased significantly when both GroEL and GroES were present compared to the reactivation with GroEL alone. With glycerol and betaine, however, GroES addition did not improve the yields achieved with GroEL and ATP alone. Since the reactivation yields were optimal with glycerol and protein reactivation did not depend on the presence of co-chaperonin, the GSΔ468 refolding under this solution condition was examined in more detail.

The present invention will be greater explained in the following examples. However, the scope of the invention is not restricted in any way by these examples.

EXAMPLE 1

Single Chaperonin Plus Osmolyte Folding

Figure 3:
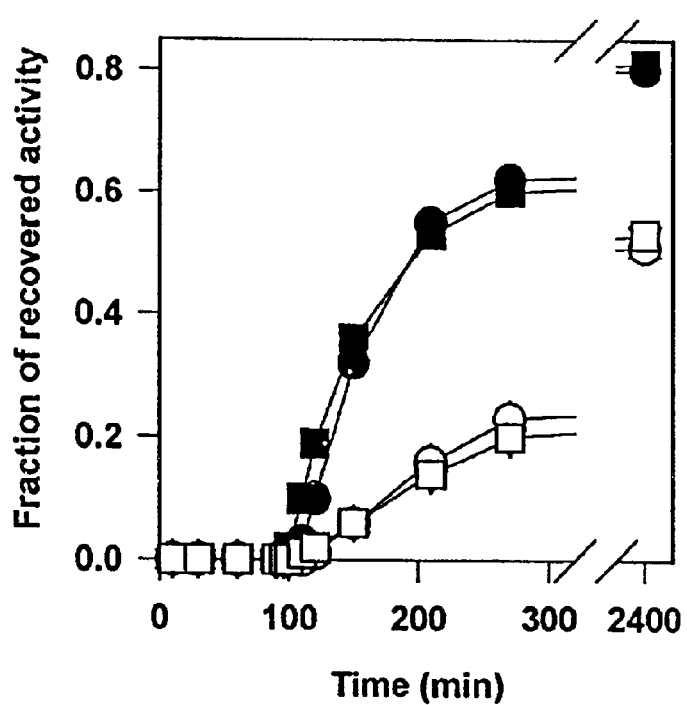
FIG. 3 shows the chaperonin-dependent renaturation of wild type and mutant GS in the presence of glycerol.

FIG. 3 shows Chaperonin-dependent renaturation of wild type and mutant GS in the presence of glycerol. Urea-denatured GS species were rapidly diluted into refolding buffer at 37° C. with either 1 μM GroEL alone (circles) or 1 μM GroEL and 2 μM GroES (squares). The activity of GS proteins was followed for 90 min. Upon the addition of 5 mM ATP and 4 M glycerol, the measurements of enzymatic activity of wild type (filled symbols) and mutant (open symbols) GS were continued. Final concentration of GS species was 0.3 μM.

In 4 M glycerol, the kinetics of chaperonin-dependent refolding of GSΔ468 was slower than that of wild type GS; after the incubation for 20 to 40 hours at 37° C. it recovered about 50% of its initial activity. Refolding kinetics of the mutant protein were similar regardless of the presence of GroES, confirming that optimal folding of the mutant could be achieved without the co-chaperonin. This illustrates that solution conditions can be found where GroES is not needed for reactivation, an important consideration for the purification of the refolded protein.

EXAMPLE 2

Concentration of Chaperonin-Protein Complexes

This method also works under conditions where larger quantities of folded product are needed. Applicants have previously demonstrated that the GroEL-protein substrate complexes can be routinely concentrated with little loss in recovery of wild type GS and rhodanese (Fisher, M. T. (1993) *J. Biol. Chem.* 268, 13777–13779; Smith, K. E. and Fisher, M. T. (1995) *J. Biol. Chem.* 270, 21517–21523, the disclosures of which are incorporated herein by reference). In the present invention, the GSΔ468-GroEL complexes were formed at an optimal substrate-to-chaperonin molar ratio (2:1) and then concentrated about 25-fold. The control experiment showed that only about 1% of the protein was lost in this concentration step. Importantly, very little spontaneous refolding occurred in glycerol solutions at this higher initial concentration of GSΔ468 (Table 2). However, after the chaperonin-GSΔ468 complexes were formed and concentrated, the refolding yields of the truncated GS mutant were as high as 67% of the original activity after 40 hours at 37° C., comparable with refolding yields of wild type GS.

TABLE 2

Refolding of GSΔ468 in 4M glycerol following concentration of GroEL-GSΔ468 complexes.

| Refolding conditions | Fraction of recovered activity | |
|---|---|---|
| | after 20 hours | after 40 hours |
| Spontaneous | 0.04 | 0.04 |
| GroEL-ATP | 0.64 | 0.67 |

EXAMPLE 3

Demonstration that Immoblized GroEL Can Function to Refold Polypeptides

Figure 5:
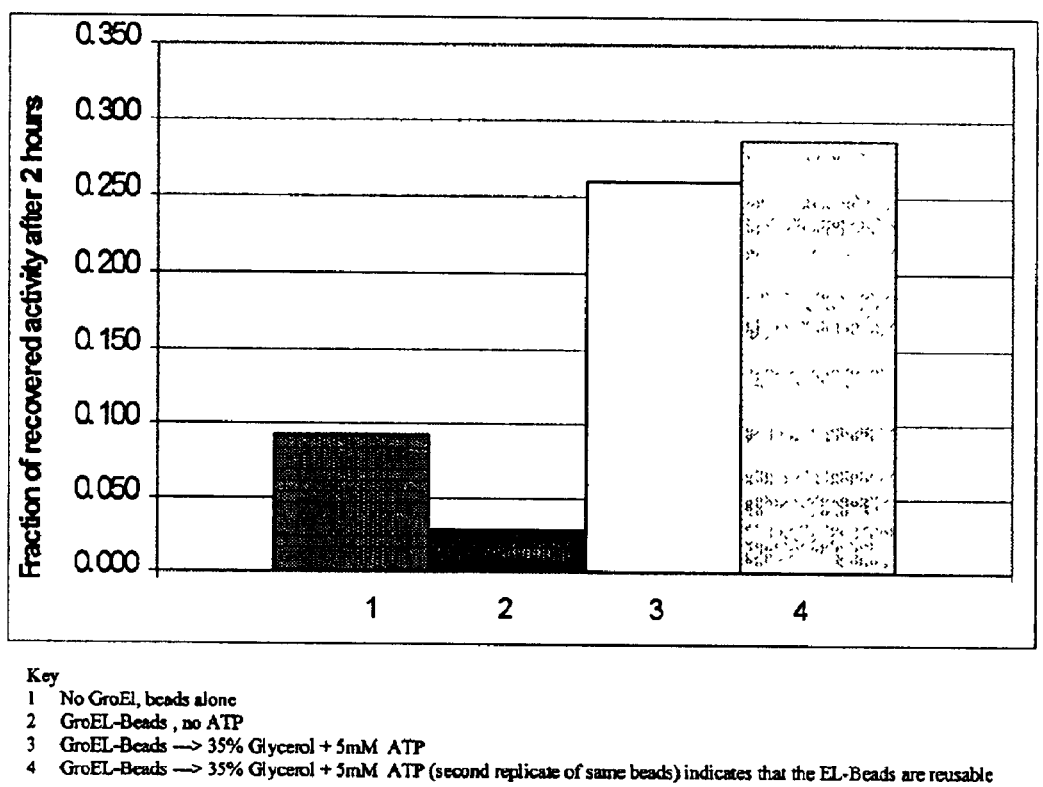
FIG. 5 shows the re-folding of malate dehydrogenase (MDH) using agarose beads upon which a chaperonin has been immobilized.

GroEL can be immobilized on inert supports (in this case agarose beads) and can bind unfolded proteins. The immobilized system functions identically to the conditions found in solution (in that addition of osmolytes promises renaturing of the chaperonin complexed proteins). FIG. 5 shows the results of the refolding of MDH using GroEL chaperonin affixed to agarose beads.

FIG. 6 shows like results for the refolding of GS on GroEL beads. Refolding of GS from immobilized chaperonin system. The immobilized chaperonin can be reused. There is no apparent decline in reactivated activity when the beads are incubated for an extra half hour at 37° C.

EXAMPLE 4

Functioning of GroEL at 1 M Urea

Figure 7:
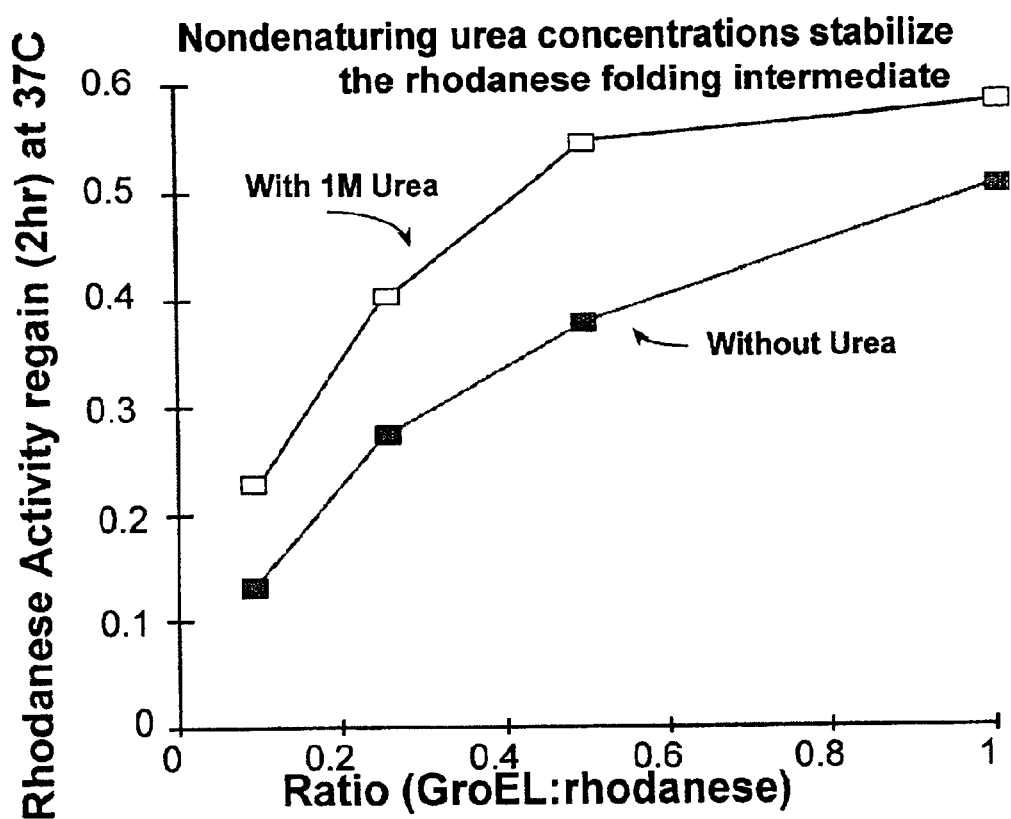
FIG. 7 shows the effectiveness of the GroEL chaperonin at elevated (1 M) concentrations of urea.

GroEL can function as an effective chaperonin in 1 M urea. FIG. 7 shows that even at the 1M urea concentration, GroEL operates to effectively assist with the refolding of the rhodanese. The unexpected synergism of the chaperonin/osmolyte system is again seen in this example.

EXAMPLE 5

Prevention of Aggregation by Osmolytes

Figure 8:
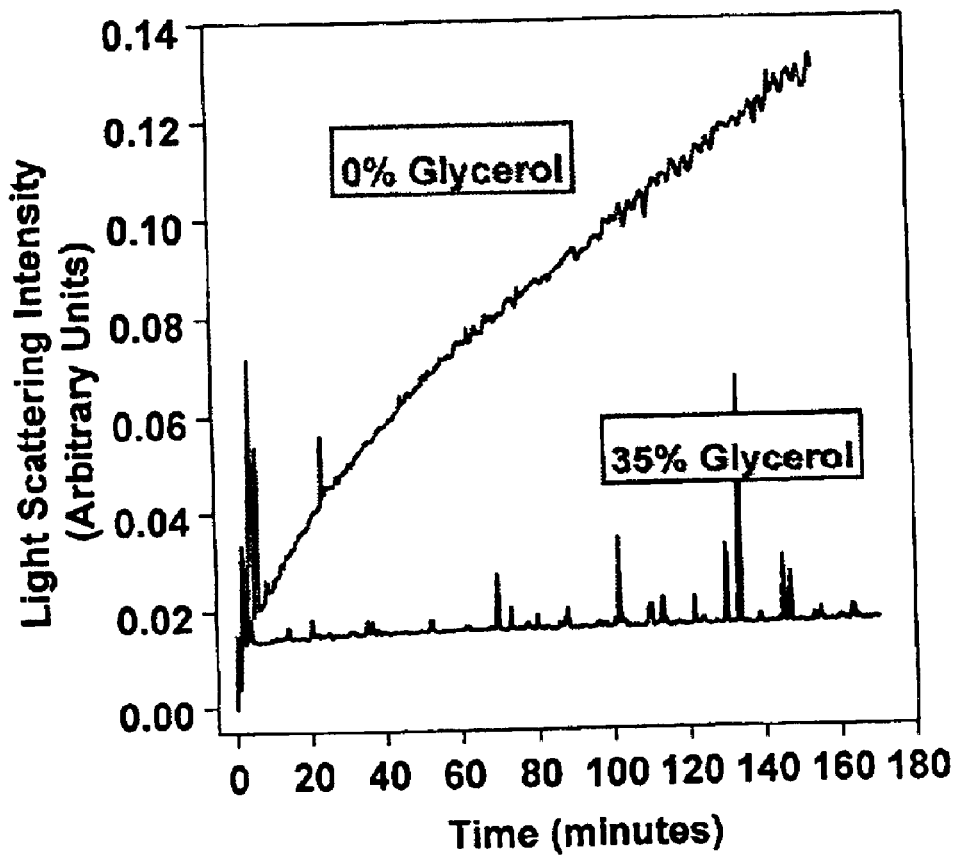
FIG. 8 shows the aggregation preventive effect of the osmolyte glycerol.
Figure 9:
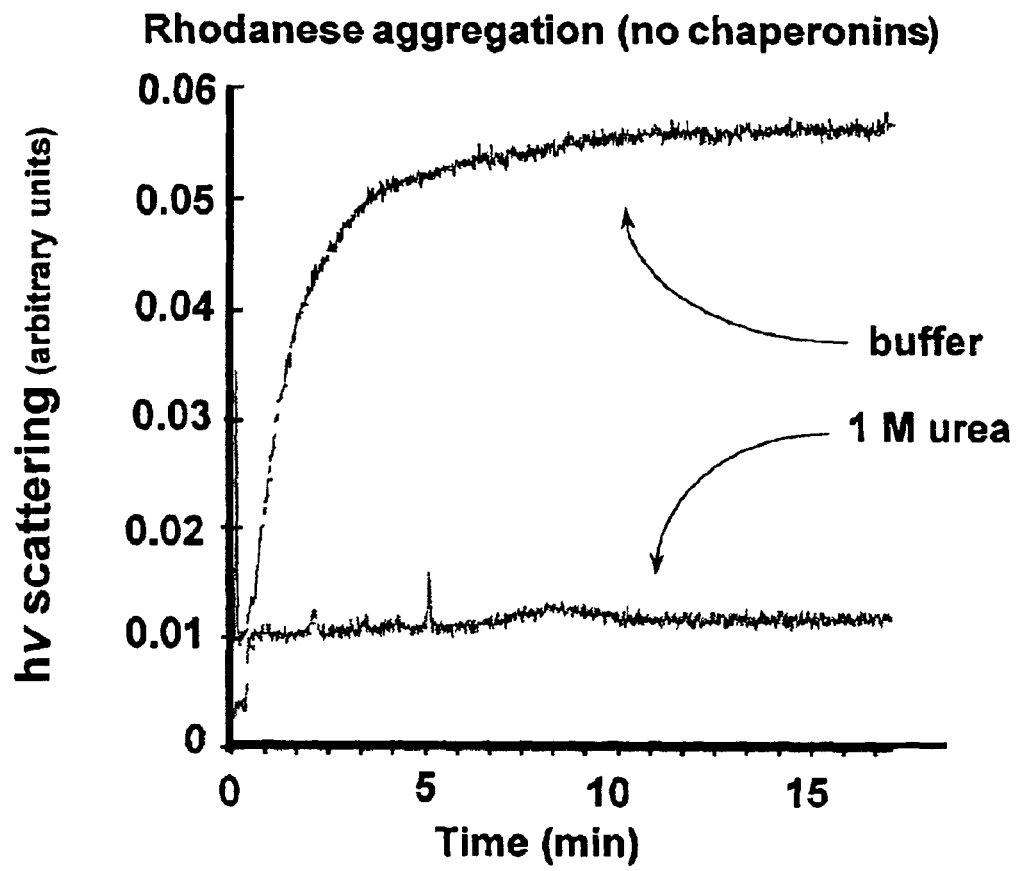
FIG. 9 shows the aggregation preventative effect of the osmolyte urea on rhodanese.

Osmolytes can prevent aggregation. For example, FIG. 8 shows that MDH is substantially prevented from aggregating into unusable forms by the addition of the osmolyte glycerol in a 35% concentration to the solution. Similarly, FIG. 9 shows significant aggregation of rhodanese being avoided by exposure to 1 M urea. These examples support the use of iterative (multiple) additions of unfolded polypeptide to increase the yield of chaperonin-protein complexes and to subsequently increase the yield of reactivable protein from the chaperonin. Because these solution conditions prevent large scale aggregation, they increase the capture efficiency of the chaperonin for the soluble partially folded or unfolded protein.

EXAMPLE 6

Chaperonin Induced Release of the Protein

Figure 10:
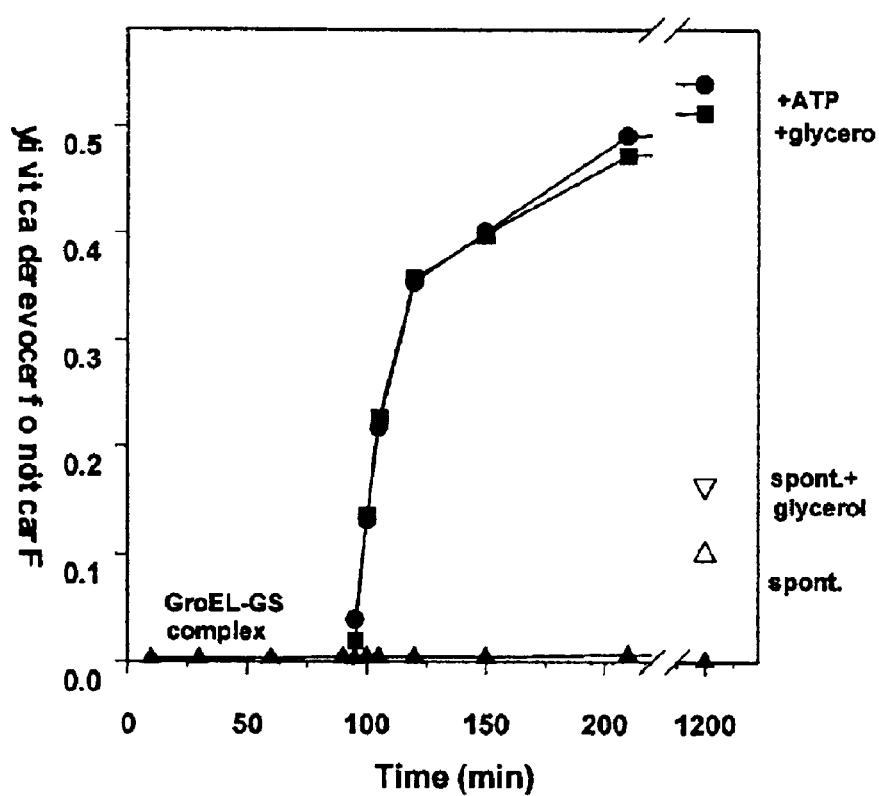
FIG. 10 shows that the osmolyte alone may be sufficient to release the protein from the chaperonin without the addition of ATP.

FIG. 10 shows another characteristic of the chaperonin/osmolyte system. It can readily be seen that the release of GS from the GroEL chaperonin was nearly identical for the chaperonin plus osmolyte combination as for the chaperonin plus osmolyte plus ATP combination. As such, the osmolyte alone can induce the release of the folded protein from the chaperonin without the aid of ATP.

EXAMPLE 7

Reduction/Oxidation Operation of Chaperonin System (No Osmolytes Present)

Figure 11:
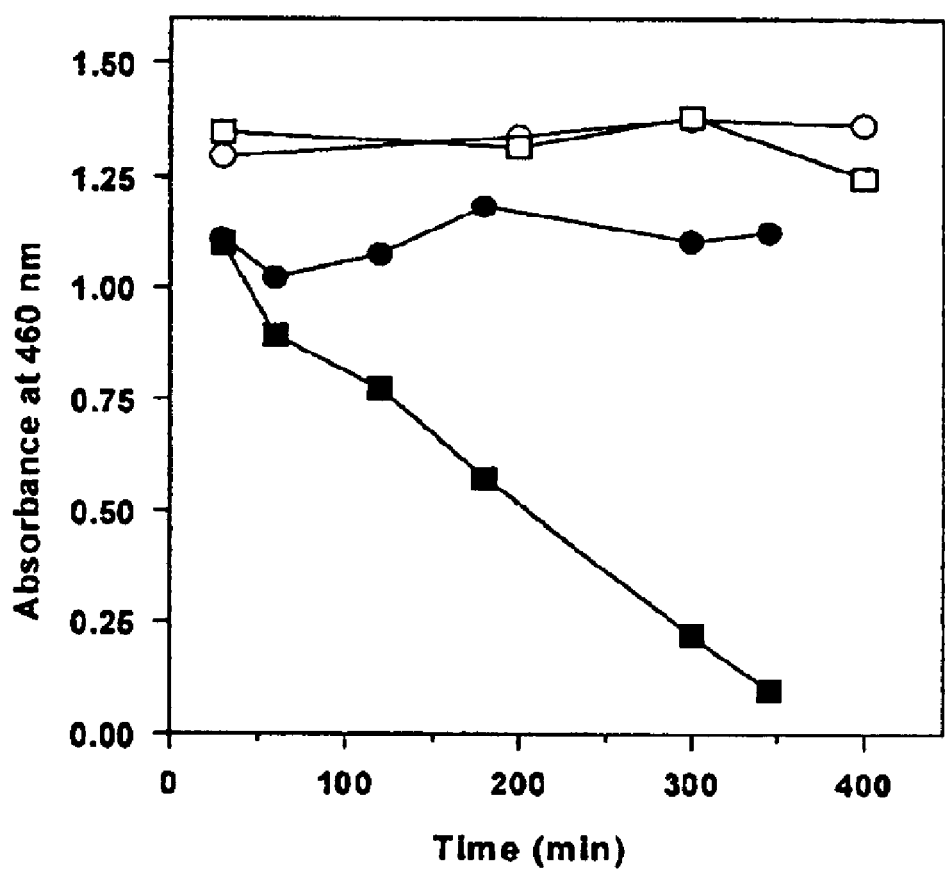
FIG. 11 shows folding of proteins using GroEL with and without the presence of oxygen.

Chaperonin refolding can be run under anaerobic conditions. FIG. 11 shows GroEL dependent reactivation of rhodanese with and without oxygen (without an osmolyte). Rhodanese (1 μM) was incubated with (■, □) or without (●, ○) 10 μM GroEL at 37° C. Data represented by open symbols were obtained under anaerobic conditions as described in Smith K. S., Voziyan P. A. and Fisher M. T., (1998) *J. Biol. Chem.* 273 28677–28681 incorporated herein by reference.

Figure 12:
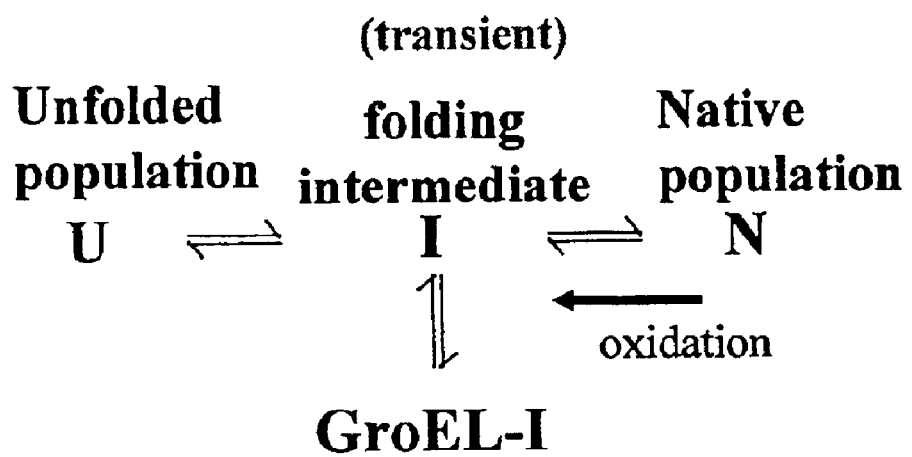
FIG. 12 illustrates the operation of the chaperonin folding mechanism with an oxidized transient intermediate.

FIG. 12 illustrates the mechanics of the oxidation reaction during the folding operation. As shown, the chaperonin binds a transient oxidized intermediate that is in equilibrium with the native folded population of proteins. Thus, the chaperonin prevents the irreversible oxidation of the folded protein from occurring and the refolding rates from the chaperonin are the same, regardless of the origin (oxidized or non-oxidized) of the intermediate.

For oxygen sensitive folding systems, a number of solution options are available to enhance the success of the chaperonin/osmolyte system. As illustrated in Example 7, the chaperonin/osmolyte system can be used in an inert oxygen free atmosphere (i.e. anaerobic atmospheres) to facilitate protein folding reactivation that is oxygen sensitive. Enhanced folding can also be insured with the osmolyte/chaperonin system by including small molecule systems such as a mixture of oxidized/reduced glutathiones and other small molecule sulfhydryl reduction/oxidation systems (e.g. dithiothreitol) to facilate disulfide bond rearrangement. Furthermore, the addition of other molecular chaperones such as protein disulfide isomerase, cis-trans peptidyl prolyl isomerases, addition chaperone proteins such as procaryotic or eucaryotic hsp70/40/grpE like systems, small heat shock proteins, and the hsp100 family can also augment the chaperonin/osmolyte system. Methionine sulfoxide reductase can be included in the system to insure that any inappropriately oxidized methionine residues are re-reduced after being the protein is released from the chaperonin/osmolyte system.

EXAMPLE 8

Use of Method on Other Substrates and with Other Osmolytes

Figure 13:
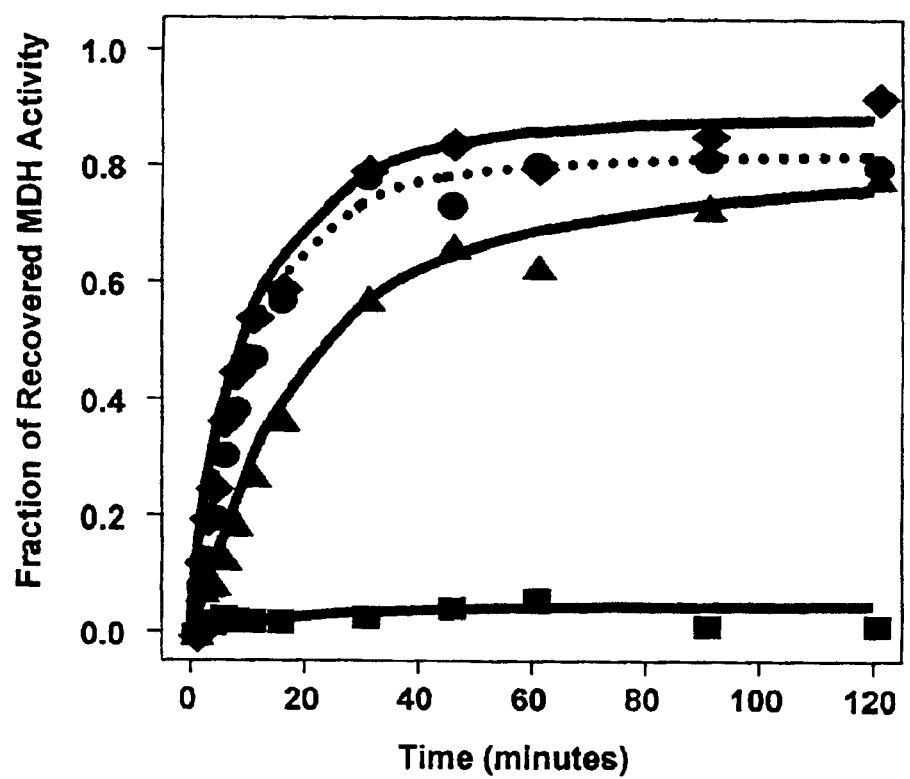
FIG. 13 shows test results for the use of MDH as a folding substrate.

The chaperonin/osmolyte method will work on other protein substrates. FIG. 13 shows the method in use to refold MDH using the GroEL chaperonin, the osmolyte glycerol and ATP (shown by filled triangle). Glycerol was used in a 35% concentration.

Also shown is the effect of GroEL alone on MDH reactivation (filled squares) which can be seen to be an arresting of the refolding process. The filled diamonds show the effect of GroES to GroEL, glycerol and ATP system. Finally, the spontaneous refolding data for MDH in the presence of 35% glycerol is shown by the filled circles. Note that except for the GroEL alone, all yield measurements are within the precision of the assay measurements.

Yield of folded protein data for refolding of MDH in the presence of chaperonins or osmolytes is shown below in Table 3. These results show that MDH can be refolded with other osmolytes besides glycerol.

TABLE 3

A comparison of MDH renaturation in the presence of GroEL/GroES ATP or with other osmolyte compounds.

| additive | percent original activity recovered* |
| --- | --- |
| GroEL/ES | 60 ± 13 |
| Glycerol (4M) | 60 ± 12 |
| Sucrose (1M) | 95 ± 8 |
| Betaine (1M) | 78 ± 30 |
| TMAO** (1M) | 36 ± 20 |

*At least 3 different series were measured with three replicates per series.
**TMAO - trimethylamine N-Oxide.

V. Screening

Figure 4:
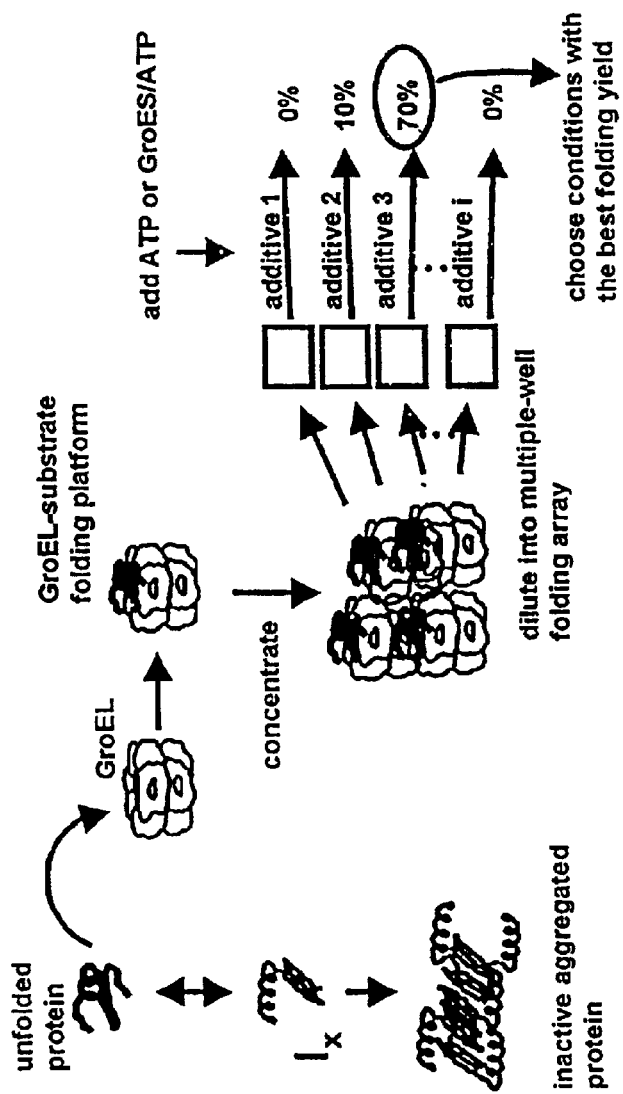
FIG. 4 depicts a schematic of a general protein folding screening system that utilizes a combination of chaperonins and osmolytes.

The process of protein folding, in both its theoretical and practical aspects, is currently the focus of intense research. Because of the inherent complexity and variability of protein structures, it is unlikely that a single universal folding methodology, applicable to all or even a majority of the proteins, could ever be devised. One only has to note that there are multitudes of folding techniques that work only with a limited number of proteins. With the increasing amount of protein sequence information available, there is the need for a rapid and efficient screening procedure to identify the optimal protein folding solutions for specific proteins of interest. FIG. 4 shows that the chaperonin/osmolyte approach offers a methodology for easy testing of a wide range of folding conditions to aid in refolding of problematic proteins. The procedure starts with the formation of GroEL-protein substrate complexes, thereby preventing non-productive aggregation. Without ATP, these complexes are very stable and can be easily concentrated with virtually no loss of the protein substrate (Fisher, M. T. (1993) *J. Biol. Chem.* 268, 13777–13779; Smith, K. E. and Fisher, M. T. (1995) *J. Biol. Chem.* 270, 21517–21523). The concentrated GroEL-protein substrate complexes are then used as a platform to test a multiple array of osmolyte solutions ("folding array") in order to identify optimal folding conditions for the protein of interest.

As each element of the folding array contains a different osmolyte solution, introducing a portion of the complex into each element of the array will test the efficacy of each osmolyte. Mutant GSΔ468 is a convenient model for the testing of the in vitro refolding procedure. Because this mutant folds to an active form in the cell, neither its folding nor its enzymatic activity have been permanently disrupted by truncation. However, the refolding of this protein in vitro represents a considerable challenge since it does not refold either spontaneously or with the major bacterial molecular chaperone systems.

Although both GroE chaperonins and cellular osmolytes have been used before individually to enhance protein folding, a combination of these methods in the two-step folding procedure provides several important and unexpected benefits. The procedure combines the chaperonin's ability to prevent aggregation and even unfold the misfolded intermediates with the inherent structural stabilization and enhancement of folding afforded through the use of osmolytes. As the experiments with GSΔ468 demonstrate in Table 1, this combination can produce a remarkable synergistic amplification of protein folding in vitro. Because the refolding of denatured protein is performed in two steps; the solution parameters such as temperature, ionic strength, and protein concentration can be adjusted independently to insure both the efficient chaperonin-substrate complex formation and the optimal substrate release and refolding in the presence of osmolytes. The high stability of the complex allows for an easy manipulation of solution conditions without the significant loss of the folding proteins due to aberrant aggregation at higher concentrations. In the case of GSΔ468, substrate concentration was initially kept low in order to avoid rapid aggregate formation and insure high chaperonin-to-substrate stoichiometry. Once the complex is formed, however, the substrate concentration can be increased to enhance the concentration-dependent second order GSΔ468 assembly reaction as shown in Table 2.

Because GroEL interacts mainly with the exposed hydrophobic surfaces of folding intermediates, it is capable of binding of a wide variety of proteins without apparent specificity (for review, see Fenton, W. A. and Horwich, A. L. (1997) *Protein Sci.* 6, 743–760). The stabilizing effect of osmolytes has been shown for a number of structurally diverse proteins and, in general, is related to the change in hydration of the macromolecular surface (Wang, A. and Bolen, D. W. (1997) *Biochemistry* 36, 9101–9108; De-Sanctis, G., Maranesi, A., Ferri, T., Poscia, A., Ascoli, F., and Santucci, R. (1996) *J. Protein. Chem.* 15, 599–606; Chen, B. L. and Arakawa, T. (1996) *J. Pharm. Sci.* 85, 419–426; Zhi, W., Landry, S. J., Gierasch, L. M., and Srere, P. A. (1992) *Protein Science* 1, 552–529). These general mechanisms of action of chaperonins and osmolytes suggest that the proposed folding method may be applicable to a relatively wide variety of proteins, regardless of their specific structural features. Indeed, besides GSΔ468, osmolyte-induced decrease in chaperonin requirements (i.e., when GroES and, in some cases, ATP were no longer required) for refolding of mitochondrial malate dehydrogenase, bovine rhodanese, and wild-type GS have been observed.

The formation of stable chaperonin-substrate complexes, the two-step refolding procedure, and a multiple-well "folding array" allow one to screen a broad range of folding solution conditions for a particular protein of interest. Unlike other screening protocols (Chen, G-Q. and Gouaux, E. (1997) *Proc. Natl. Acad. Sci. USA* 94, 13431–13436, the disclosure of which is incorporated herein by reference), methods of the present invention ensures that initial aggregation of now stable protein folding intermediate does not occur. For the screening, protein folding efficiency could be monitored either by measuring protein enzymatic activity or by following spectroscopic or other structurally sensitive parameters that characterize protein conformation. In an earlier study, the matrix-immobilized GroEL-GS and GroEL-tubulin complexes were used to refold corresponding proteins (Phadtare, S., Fisher, M. T., Yarbrough, L. R. (1994) *Biochim. Biophys. Acta.* 1208, 189–192, the disclosure of which is incorporated herein by reference). In these cases, however, problems with protein release and aggregation limited the broad applicability of the technique (Phadtare, S., Fisher, M. T., Yarbrough, L. R. (1994) *Biochim. Biophys. Acta.* 1208, 189–192). Coupling of this technique with the chaperonin/osmolyte folding array approach potentially allows one to obtain preparative quantities of the protein of interest using column chromatography. In another solid support-based approach the attachment of protein substrate to the matrix was achieved using the monomeric fragments of GroEL apical domains (Altamirano, M. M., Golbik, R., Zahn, R., Buckle, A. M., and Fersht, A. R. (1997) *Proc. Natl. Acad. Sci USA* 94, 3576–3578; Altamirano, M. M., Garcia, C., Possani, L. D., and Fersht, A. R. (1999) *Nat. Biotechnol.* 17, 187–191). Although these "mini-chaperones" can enhance protein refolding in some cases (Zahn, R., Buckle, A. M., Perrett, S., Johnson, C. M., Corrales, F. J., Golbik, R., and Fersht, A. R. (1996) *Proc. Natl. Acad. Sci. USA* 93, 15024–15029, the disclosure of which is incorporated herein by reference), they completely fail to arrest protein folding and cannot substitute for oligomeric GroEL in the enhancement of folding (Weber, F., Keppe, F., Georgopoulos, C., Hayer-Hartl, M. K., and Hartl, F. U. (1998) *Nat. Struct. Biol.* 5, 977–985, the disclosure of which is incorporated herein by reference). It appears, therefore, that the use of the oligomeric GroEL chaperonin is better suited for capturing, stabilizing, and immobilizing aggregation-prone protein substrates on a matrix where optimal solution conditions for successful release and refolding can be tested in a broad manner. As this invention with GSΔ468 demonstrates, at certain solution conditions GroES can be completely removed from the folding protocol without compromising folding yields, an important consideration when a large-scale refolding and purification procedures have to be performed.

Although the model protein GSΔ468 folded successfully in cellular environment, it failed to refold with bacterial GroE and DnaK chaperone systems in vitro. These data imply that cytosol components other than the above molecular chaperones could be essential for productive folding of mutant GS. It is certainly possible that the low molecular weight solutes within the bacterial cytoplasm may play a significant role in facilitating protein folding. Indeed, one of the compounds that enhanced chaperonin-dependent GSΔ468 refolding in our experiments was 0.5 M potassium glutamate. These conditions are particularly interesting because the physiological concentration of potassium and glutamate ions in *E. coli* cells has been shown to be in a range of 0.2–1 M (Richey, B., Cayley, D. S., Mossing, M. C., Kolka, C., Anderson, C. F., Farrar, T. C., and Record, M. T., Jr. (1987) *J. Biol. Chem.*, 262, 7157–7164, the disclosure of which is incorporated herein by reference). It is possible that the other natural osmolytes found in many bacterial, plant, and mammalian cells (Sola-Penna, M., Ferreira-Pereira, A., Lemos, A. P., and Meyer-Fernandes, J. R. (1997) *Eur. J. Biochem.* 248, 24–29; Yoshiba, Y; Kiyosue, T; Nakashima, K; Yamaguchi-Shinozaki, K; Shinozaki, K (1997) *Plant. Cell. Physiol.* 38, 1095–10102; Paredes, A; McManus, M; Kwon, H M; Strange, K. (1992) *Am. J. Physiol.* 263, C1282–1288; Warskulat, U; Wettstein, M; Haussinger, D (1997) *Biochem. J.* 321, 683–690; Record, M. T., Jr., Courtenay, E. S., Cayley, S., and Guttman, H. J. (1998) *Trends Biochem. Sci.* 23, 190–194, the disclosures of which are incorporated herein by reference), in conjunction with molecular chaperones, could also enhance the intracellular protein folding kinetics and stability, and may represent a more complete system that describes protein folding mechanism in the cell. For example, TMAO, a natural osmolyte found in a number of marine species (Yancey, P. H., Clark, M. E., Hand, S. C., Bowlus, R. D., and Somero, G. N. (1982) *Science* 217, 1214–1222), facilitates the refolding of GSΔ468 in the presence of chaperoning.

The evolutionary selected cellular solution conditions arguably represent the best system for folding the intrinsic proteins. The present invention demonstrates that a combination of two natural cellular components, chaperonins and osmolytes, can dramatically improve folding yields for a protein whose in vitro folding reaction is problematic.

While the present invention has been described herein with reference to the particular embodiments thereof, a latitude of modifications, various changes and substitutions are intended in the foregoing disclosure, and it will be appreciated that some features of the invention will be employed without a corresponding use of other features, without departing from the scope of the invention as set forth.

What we claim is:

1. A method of folding a denatured polypeptide, comprising the steps of:
   (a) providing a polypeptide in an unfolded state which is capable of binding to a chaperonin;
   (b) binding said polypeptide to said chaperonin to form a chaperonin-polypeptide complex for the folding of said polypeptide to its biologically active state; and
   (c) adding an osmolyte to said chaperonin-polypeptide complex, thereby promoting the folding of said polypeptide from its unfolded state to its folded state to yield a folded biologically active polypeptide whereby said promoting is greater than that which is achieved using chaperonins and osmolytes alone.

2. The method of folding a denatured polypeptide of claim 1 wherein said chaperonin is of the *Escherichia coli* GroE chaperonin family.

3. The method of folding polypeptides of claim 2 in which the chaperonin is *E. coli* GroEL.

4. The method of folding polypeptides of claim 1 in which the osmolyte is sucrose.

5. The method of folding polypeptides of claim 1 in which the osmolyte is glycerol.

6. The method of folding polypeptides of claim 1 in which the osmolyte is trimethylamine N-oxide.

7. The method of folding polypeptides of claim 1 in which the osmolyte is potassium glutimate.

8. The method of folding polypeptides of claim 1 in which the osmolyte is arginine.

9. The method of folding polypeptides of claim 1 in which the osmolyte is betaine.

10. The method of folding polypeptides of claim 1 in which the osmolyte is urea.

11. The method of folding polypeptides of claim 1 in which the osmolyte is sarcosine.

12. The method of folding polypeptides of claim 1 further comprising the step of promoting the folding of said polypeptide by the addition of a co-chaperonin to the chaperonin-polypeptide complex.

13. The method of folding polypeptides of claim 1 wherein said chaperonin is immobilized on an inert support.

14. The method of folding polypeptides of claim 1 wherein the concentration of said osmolyte is sufficient to reduce the aggregation of unfolded polypeptides into unusable forms.

15. The method of folding polypeptides of claim 1 wherein said polypeptide is substantially incapable of being folded to its biologically active form by either a chaperonin or an osmolyte alone.

16. The method of folding a denatured polypeptide of claim 1 wherein said method is conducted under controlled oxidation/reduction conditions.

17. The method of folding a denatured polypeptide of claim 16 in which the oxidation/reduction conditions comprise an at least substantially anaerobic environment.

18. The method of folding a polypeptide of claim 16 wherein said oxidation/reduction conditions are controlled by one or more redox agents selected from the group comprising glutathione, sulfhydryl and protein reduction systems.

19. A method of folding a denatured polypeptide, comprising the steps of:
    (a) providing a polypeptide in an unfolded state that is capable of binding to an oligomeric chaperonin;

(b) binding said polypeptide to said chaperonin to form a chaperonin-polypeptide complex for the folding of said polypeptide to its biologically active state; and (c) adding an osmolvte to said chaperonin-polypeptide complex, thereby promoting the folding of said polypeptide from its unfolded state to its folded state to yield a folded biologically active polypeptide whereby said promoting is greater than that which is achieved using chaperonins and osmolytes alone.

20. The method of folding a denatured polypeptide of claim 19 wherein said chaperomn is of the *Escherichia coli* GroE chaperonin family.

21. The method of folding polypeptides of claim 20 in which the chaperonin is *E. coli* GroEL.

22. The method of folding polypeptides of claim 19 in which the osmolyte is urea.

23. The method of folding polypeptides of claim 19 further comprising the step of promoting the folding of said polypeptide by the addition of a co-chaperonin to the chaperonin-polypeptide complex.

24. The method of folding polypeptides of claim 19 further comprising a step of removing a metastable polypeptide folding intermediate prior to complete folding of the polypeptide and further stabilizing said metastable polypeptide.

25. The method of folding polypeptides of claim 19 wherein said chaperonin is immobilized on an inert support.

26. The method of folding polypeptides of claim 19 wherein the concentration of said osmolyte is sufficient to reduce the aggregation of unfolded polypeptides into unusable forms.

27. The method of folding a denatured polypeptide of claim 19 wherein said method is conducted under controlled oxidation/reduction conditions.

28. The method of folding a denatured polypeptide of claim 27 in which the oxidation/reduction conditions comprise an at least substantially anaerobic environment.

29. The method of folding a polypeptide of claim 27 wherein said oxidation/reduction conditions are controlled by one or more redox agents selected from the group comprising glutathione, sulfhydryl and protein reduction systems.

* * * * *

UNITED STATES PATENT AND TRADEMARK OFFICE
CERTIFICATE OF CORRECTION

PATENT NO. : 6,887,682 B2
DATED : May 3, 2005
INVENTOR(S) : Fisher et al.

It is certified that error appears in the above-identified patent and that said Letters Patent is hereby corrected as shown below:

Column 4,
Line 51, delete "lease" and insert -- least -- therefor.

Column 5,
Line 16, delete "50 MM" and insert -- 50 mM -- therefor.

Column 14,
Lines 23, 25, 29, 31, 33, 35, 37, 39, 45 and 49, insert -- a denatured -- between "folding" and "polypeptide".
Line 42, insert -- , wherein said co-chaperonin has the ability to bind and dissociate from the chaperonin and aid said chaperonin to achieve correct binding of said polypeptide -- before ".".
Line 64, delete "comprising" and insert -- consisting of -- therefor.

Column 15,
Lines 13, 15, 17 and 21, insert -- a denatured -- between "folding" and "polypeptide".

Column 16,
Lines 4, 6 and 16, insert -- a denatured -- between "folding" and "polypeptide".

Signed and Sealed this

Eleventh Day of October, 2005

JON W. DUDAS
*Director of the United States Patent and Trademark Office*